(12) United States Patent
Han

(10) Patent No.: US 10,383,773 B2
(45) Date of Patent: Aug. 20, 2019

(54) MEDICAL CAST AND SKIN PROTECTOR

(71) Applicant: Jong Kun Han, Seoul (KR)

(72) Inventor: Jong Kun Han, Seoul (KR)

( * ) Notice: Subject to any disclaimer, the term of this patent is extended or adjusted under 35 U.S.C. 154(b) by 612 days.

(21) Appl. No.: 15/031,890

(22) PCT Filed: Oct. 23, 2014

(86) PCT No.: PCT/KR2014/009990
§ 371 (c)(1),
(2) Date: Apr. 25, 2016

(87) PCT Pub. No.: WO2015/068975
PCT Pub. Date: May 14, 2015

(65) Prior Publication Data
US 2016/0262945 A1 Sep. 15, 2016

(30) Foreign Application Priority Data
Nov. 7, 2013 (KR) .................. 10-2013-0134629

(51) Int. Cl.
*A61F 5/01* (2006.01)
*A61F 13/00* (2006.01)
(Continued)

(52) U.S. Cl.
CPC .............. *A61F 13/046* (2013.01); *A61F 5/01* (2013.01); *A61F 5/0111* (2013.01);
(Continued)

(58) Field of Classification Search
CPC .. A61F 13/046; A61F 5/05866; A61F 5/0585; A61F 13/00059; A61F 5/0111; A61F 13/0206; A61F 5/0118; A61F 5/01
See application file for complete search history.

(56) References Cited

U.S. PATENT DOCUMENTS 4,019,506 A * 4/1977 Eschmann .............. A61F 13/04
602/8

5,016,622 A * 5/1991 Norvell ................. A61F 13/041
602/20

(Continued)

FOREIGN PATENT DOCUMENTS

CN 1633951 7/2005
CN 101199366 6/2008
(Continued)

OTHER PUBLICATIONS

EPO, Extended European Search Report of EP 14859732.1 dated May 11, 2017.
SIPO, Office Action of CN 201480059743.4 dated Dec. 2, 2016.

*Primary Examiner* — Tarla R Patel
(74) *Attorney, Agent, or Firm* — Lex IP Meister, PLLC

(57) ABSTRACT

The present invention relates to a medical cast having a dual structure. The present invention provides the medical cast comprising: a skin protector coming into contact with the affected area of a patient, woven by mixing and using at least two kinds of functional fibers in order to increase adhesive strength with the skin, and manufactured such that diamond-shaped mesh holes are formed in the shape of a meshed net; an inner supporting cast formed to cover the outer side of the skin protector and comprising an inside supporting cast for absorbing sweat or body waste between the casts, an inner ventilating channel for covering the outer surface of the inside supporting cast and improving air permeability, an adhesion enhancing part for increasing the elasticity of the cast, and an inner rigidity reinforcing part for providing primary rigidity for the medical cast; and an outer supporting cast formed to cover the outer side of the inner supporting cast, impregnated with a hardening solution having hydraulic properties, and comprising an outer ventilating channel formed along the circumference thereof, an adhesion enhancing part connected with the outer ventilating channel so as to provide predetermined elastic force, a cutter part provided on one surface of the outer side thereof for guiding the progressing direction of a cutter blade, and outer (Continued)

rigidity reinforcing parts formed on both sides of the cutter part so as to provide secondary rigidity for the medical cast.

15 Claims, 8 Drawing Sheets

(51) Int. Cl.
*A61F 13/02* (2006.01)
*A61F 13/04* (2006.01)
*A61F 5/058* (2006.01)

(52) U.S. Cl.
CPC .......... *A61F 5/0118* (2013.01); *A61F 5/0585* (2013.01); *A61F 5/05866* (2013.01); *A61F 13/00059* (2013.01); *A61F 13/0206* (2013.01)

(56) References Cited

U.S. PATENT DOCUMENTS

| | | | |
|---|---|---|---|
| 6,042,557 A * | 3/2000 | Ferguson | A61F 5/058 602/5 |
| 6,547,751 B1 | 4/2003 | Barberio | |
| 8,303,527 B2 * | 11/2012 | Joseph | A61F 5/01 602/8 |
| 9,561,128 B2 * | 2/2017 | Joseph | A61F 5/01 |
| 2006/0155226 A1 * | 7/2006 | Grim | A61F 5/01 602/6 |
| 2011/0224590 A1 | 9/2011 | Jensen | |
| 2011/0245746 A1 | 10/2011 | Lee | |
| 2014/0171837 A1 * | 6/2014 | Harcourt | A61F 5/05833 601/7 |

FOREIGN PATENT DOCUMENTS

| | | |
|---|---|---|
| JP | 05-154174 | 6/1993 |
| KR | 20-0346054 | 3/2004 |
| KR | 10-0792252 | 1/2008 |
| KR | 10-2011-0006100 | 1/2011 |
| KR | 10-2012-0120536 | 11/2012 |
| WO | 2004/112671 | 12/2004 |
| WO | 2006/027763 | 3/2006 |

* cited by examiner

[FIG. 1]
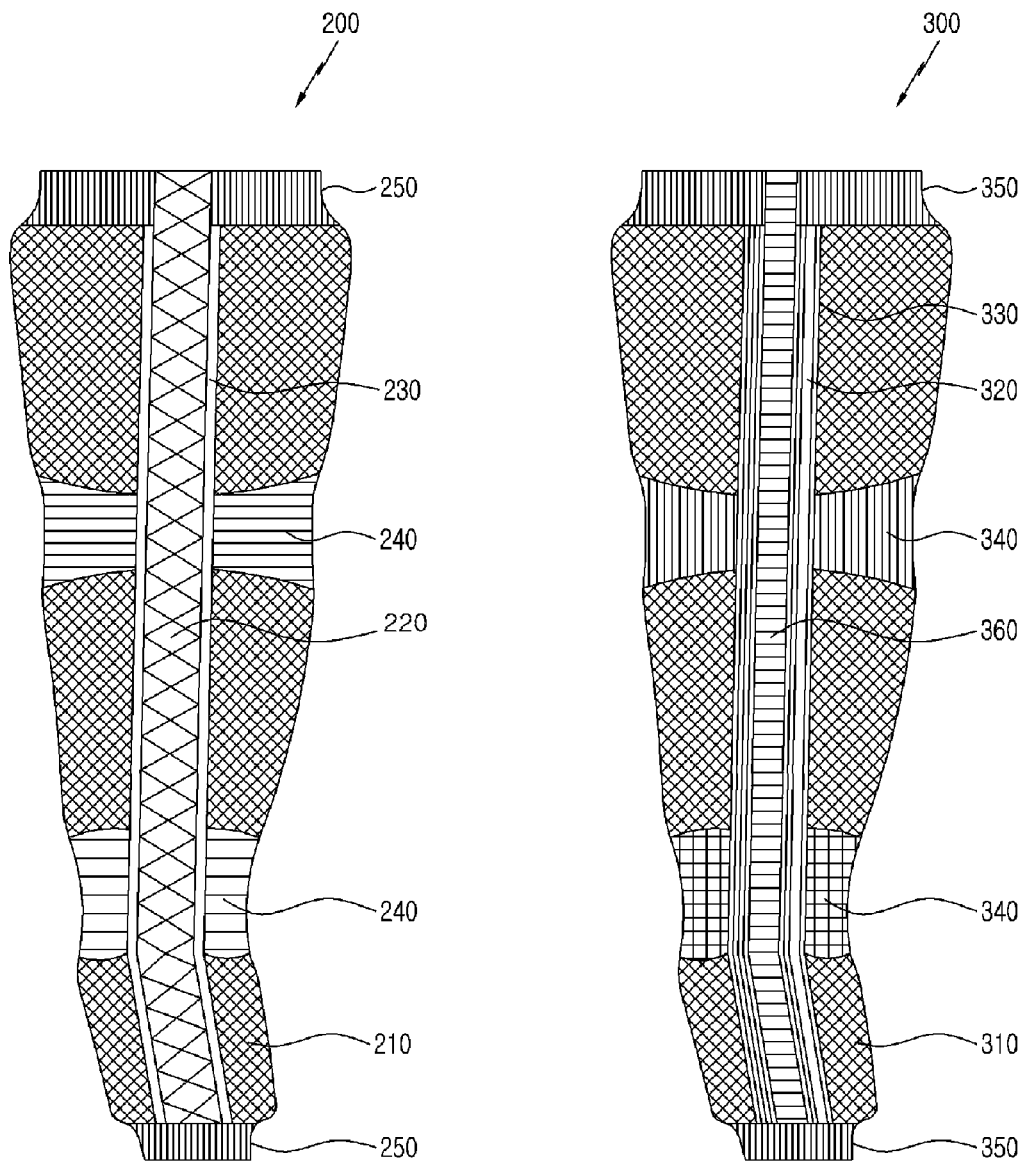

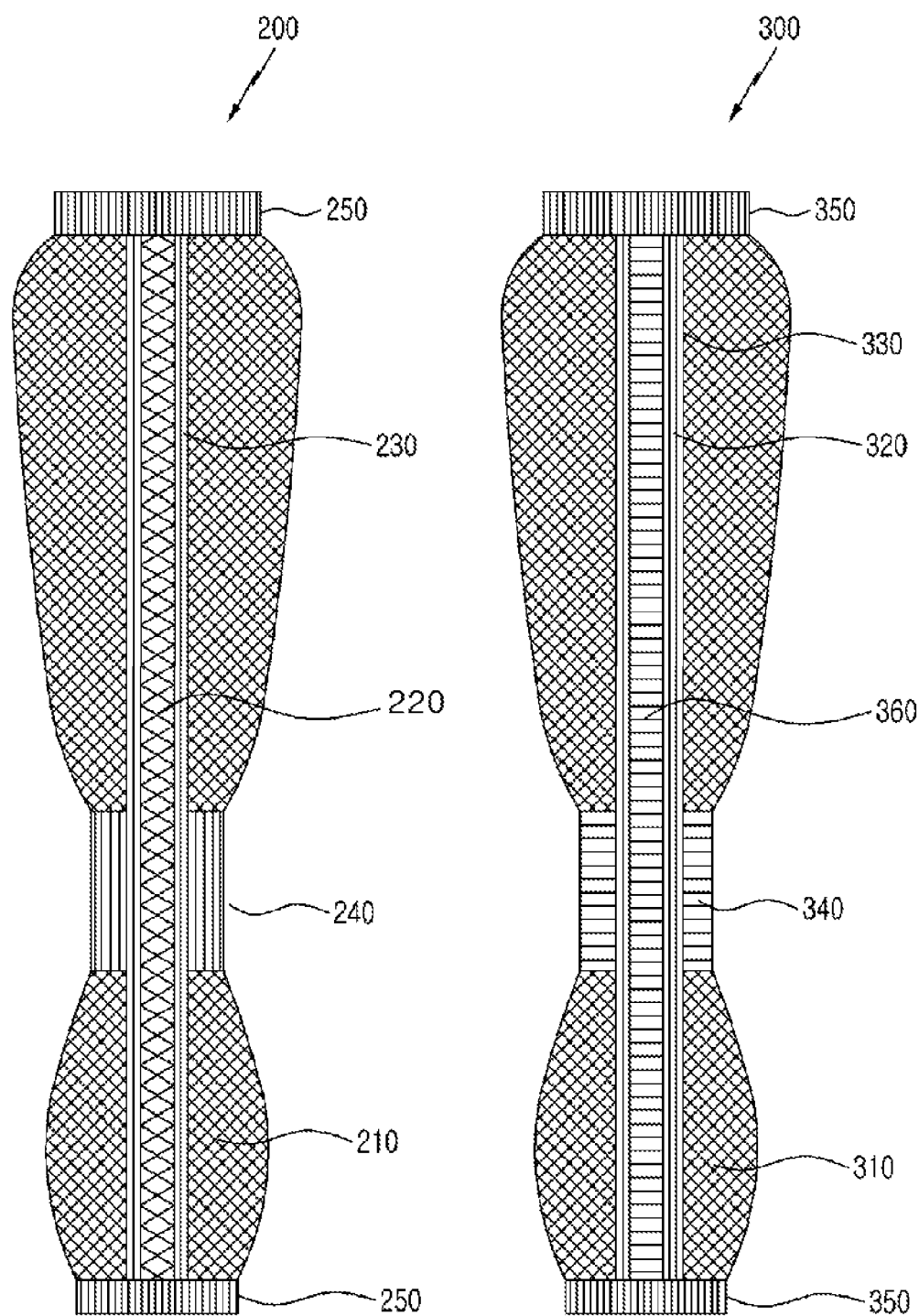
[FIG. 2]

[FIG. 3]
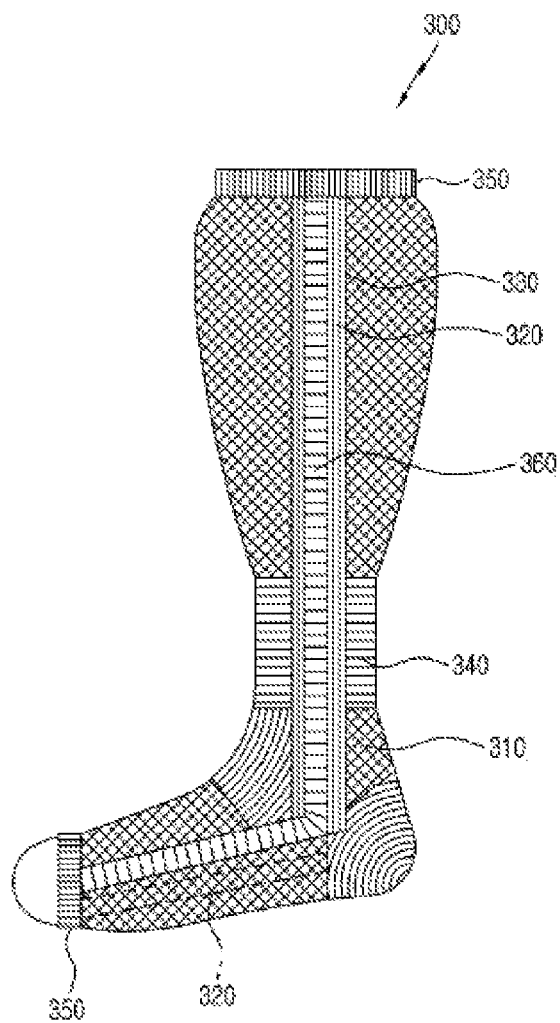

[FIG. 4]
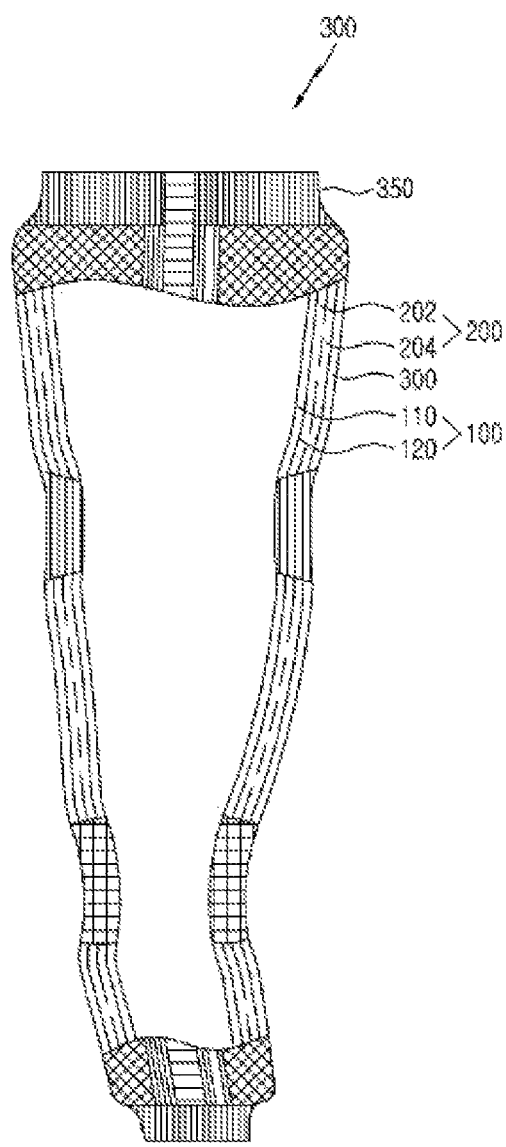

[FIG. 5]
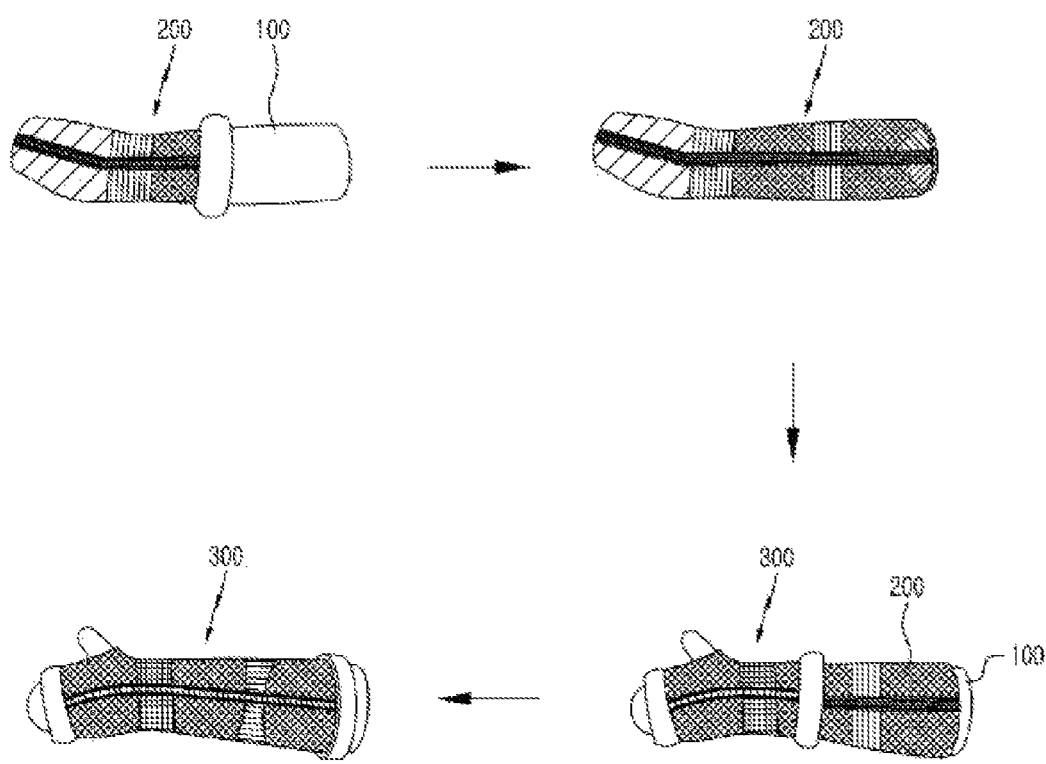

[FIG. 6]
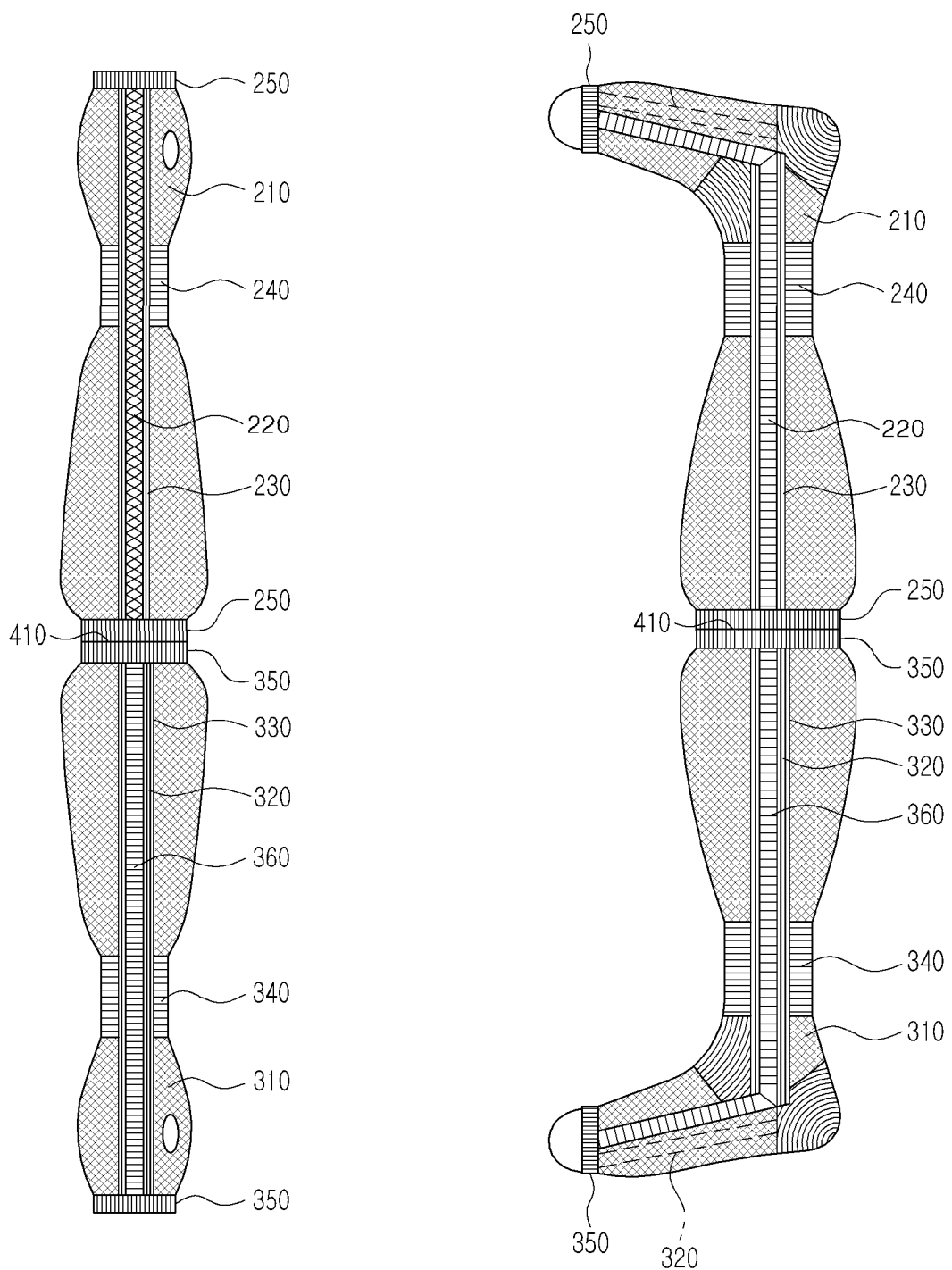

[FIG. 7]
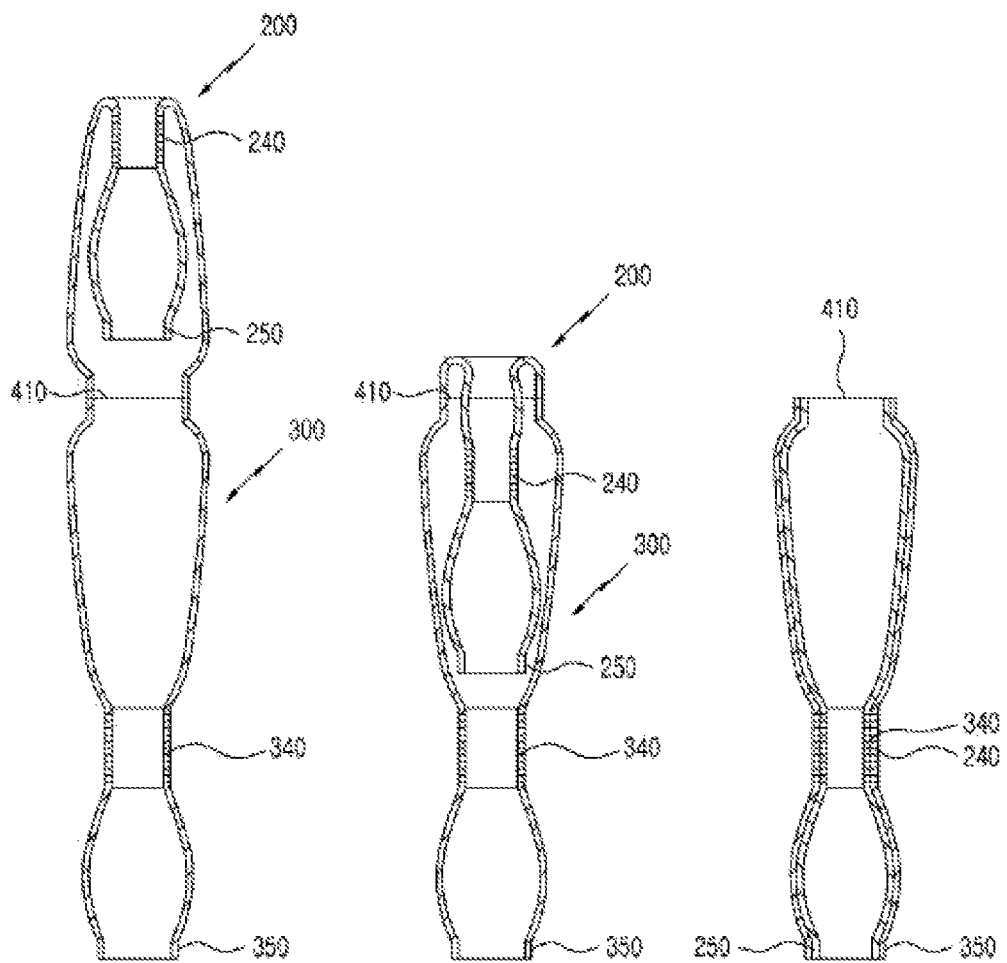

[FIG. 8]
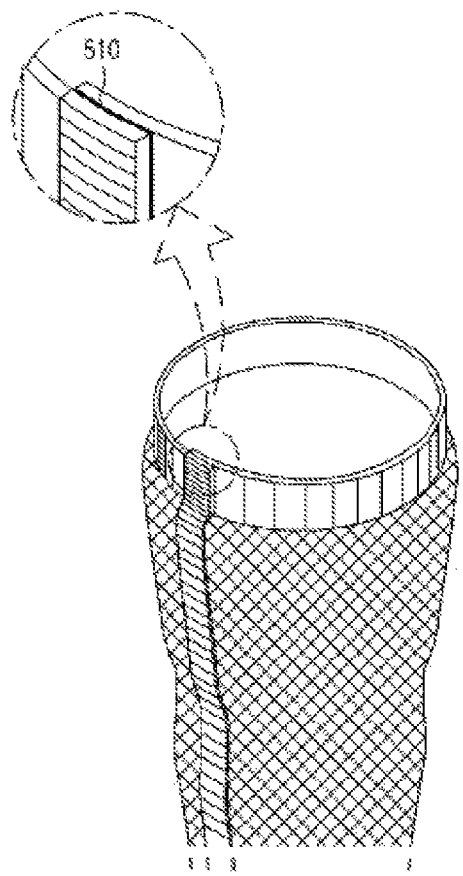

MEDICAL CAST AND SKIN PROTECTOR

TECHNICAL FIELD

The present invention relates to a medical cast having a dual structure. More particularly, the present invention relates to a medical cast having a dual structure, which has a ventilation channel so as to achieve excellent air permeability, is manufactured by using a special thread material to easily discharge moisture and provide excellent permeability, thereby improving X-Ray permeability, has strong adhesive force so as to prevent a bending phenomenon at each joint and each bent portion of a human body, and can sufficiently endure a weight of the human body by providing a stiffness strengthening means in a support and a skin protector.

BACKGROUND ART

In general, a cast operation of a bone-fracture patient is treated by a method which covers a skin prevention cloth (stockinet) on a contact portion with a skin, winds a cotton bandage thereon, and thereafter, winds and hardens a plaster bandage or water wetting casting table several times.

However, in the case of the cast operation, since the cotton bandage is wound on the skin prevention cloth in a spiral shape with a predetermined thickness repeatedly several times, sweat generated from an affected area is not smoothly discharged while air permeability deteriorates, and as a result, a patient feels urtication and stuffiness, and there is a disadvantage in that it is highly concerned to develop a secondary infection, such as, skin erosion and bubbles.

In particular, in the cast operation, a setting solution is impregnated in a thin tape type glass fiber or polyester yarn to be superimposed on the affected area by using cast cotton yarn, the thin tape type glass fiber or polyester yarn is wound at a wound pressure or thickness which is irregular according to an operation method of an operator, and as a result, the patient receives not a uniform pressure but partially different pressures to cause poor blood circulation and since the operation is complicated and air permeability with the skin is not almost provided due to the use of the stockinet and the cotton bandage as the skin protector, there are a lot of problems including urtication and stuffiness, uncleanliness, a horrible stench, and the like.

As a result, Korean Patent Registration No. 0693221 (Mar. 5, 2007) discloses a skin protector of a cast for solving the aforementioned problem. The prior art has a sack shape suitable for a bending shape of the affected area of a human body based on the shape of a sheet on which a non-porous film and a porous film are stacked above and below polyurethane foam while providing multiple independent cells throughout a whole area and the sack shape based on the sheet shape is configured by a long glove shape in which a thumb and four remaining fingers can be inserted and which has both ends perforated and elongates toward the back of a hand and an elbow while covering a wrist portion.

However, in the medical cast in the related art, since after the operation, it is difficult to secure the air permeability, and as a result, the patient cannot but suffer from pain and should wear the cast for a long time, moisture such as the sweat, or the like generated from a cast portion is not smoothly discharged, therefore, a serious bad smell and an injury such as a skin rash, or the like are accompanied, and while continuously feeling the weight of a human body, damage or breakage occurs on a surface layer of the cast, and as a result, treatment efficiency of the cast remarkably deteriorates.

DISCLOSURE

Technical Problem

In order to solve the problem, the present invention has been made in an effort to more conveniently perform an operation of a cast by manufacturing a medical cast used in an orthopedic surgery or an emergency treatment cast in a dually configured stocking type, significantly shorten an operation time of the medical cast by improving operation accuracy, and provide comfortable wearing feeling by providing an even pressure regardless of an affected area of a patient.

Further, the present invention has been made in an effort to easily discharge moisture by forming a ventilating channel so as to achieve excellent air permeability, provide excellent permeability by being manufactured by using a special cotton yarn material, and thus, easily verify a progress status of minute bone union by improving X-ray permeability.

In addition, the present invention has been made in an effort to provide adhesive strength so as to prevent the bending phenomenon of each joint and bent portion of a human body and sufficiently endure a weight of the human body by configuring a rigidity reinforcing means in a support and a skin protector to allow a user to more conveniently use the medical cast.

Moreover, the present invention has been made in an effort to interrupt occurrence of secondary infection by preventing an injury which occurs on the skin of the patient by a cutter blade at the time of removing the cast and an injury which occurs due to direct friction between the medical cast and the skin.

Besides, the present invention has been made in an effort to provide the medical cast manufactured in a stocking type and manufacture the medical cast with various patterns and colors to provide a medical cast having a more excellent aesthetic sense.

Technical Solution

In order to achieve the object, the present invention provides a medical cast comprising: a skin protector coming into contact with the affected area of a patient, woven by mixing and using at least two kinds of functional fibers in order to increase adhesive strength with the skin, and manufactured such that diamond-shaped mesh holes are formed in the shape of a meshed net; an inner supporting cast formed to cover the outer side of the skin protector and comprising an inside supporting cast for absorbing sweat or body waste between the casts, an inner ventilating channel for covering the outer surface of the inside supporting cast and improving air permeability, an adhesion enhancing part for increasing the elasticity of the cast, and an inner rigidity reinforcing part for providing primary rigidity for the medical cast; and an outer supporting cast formed to cover the outer side of the inner supporting cast, impregnated with a hardening solution having hydraulic properties, and comprising an outer ventilating channel (310) formed along the circumference thereof, an adhesion enhancing part connected with the outer ventilating channel (310) so as to provide predetermined elastic force, a cutter part provided on one surface of the outer side thereof for guiding the progressing direction of a cutter blade, and outer rigidity reinforcing parts formed on both sides of the cutter part so as to provide secondary rigidity for the medical cast.

Further, provided is a medical cast, in which the inner and outer ventilating channels may be formed by the meshed net-shaped diamond-shaped mesh holes and the mesh holes may be manufactured with an area of 0.6 mm and 0.2 to 0.5 mm, respectively.

In addition, provided is a medical cast, spinning ends formed by span yarn to provide a predetermined elastic pressure may be configured on upper and lower ends of the outer supporting cast.

Moreover, provided is a medical cast, in which the inner rigidity reinforcing unit may further include inner molding units to be fixed with the inner ventilating channel and the inner supporting cast on both sides thereof.

Besides, provided is a medical cast, in which the outer rigidity reinforcing unit may further include outer molding units to be fixed with the outer ventilating channel and the cutter part on both sides thereof.

Further, provided is a medical cast, in which two or more of a color, a phrase, and a decoration may be configured on the surface of the outer supporting cast.

In addition, provided is a medical cast, in which the inner supporting cast and the outer supporting cast may be integrally connected to each other by a connection line so as to have opposite locations to each other to be symmetric to each other.

Moreover, provided is a medical cast, in which a detachable unit having predetermined adhesive strength may be configured in any one of the inner supporting cast and the outer supporting cast to be worn while covering the affected area of the patient.

Besides, provided is a medical cast, in which the inner supporting cast and the outer supporting cast may be manufactured in any one of a pipe shape, a heck-shape, a trapezoidal shape, a pot shape, a fan shape, a tube type, an arm type, and a leg shape according to a body structure of the patient.

Further, provided is a medical cast, in which the skin protector may be constituted by an inner layer which comes in direct contact with the skin of the patient and an outer layer which comes in contact with cotton yarn forming an inner surface of any one of the inner supporting cast and the outer supporting cast.

Besides, provided is a medical cast, in which the skin protector and the inner and outer supporting casts may be combined with a sterilizer and an antibacterial agent and mixed with a waterproof agent in order to prevent micro bacteria from being grown.

Moreover, provided is a medical cast, in which the functional fiber may be any one of polyester yarn, span covering yarn, polyolefin, polypropylene yarn, gore tex, and olefin yarn.

Advantageous Effects

According to the present invention, it is possible to easily discharge moisture by forming a ventilating channel so as to achieve excellent air permeability, provide excellent permeability by being manufactured by using a special cotton yarn material, and thus, easily verify a progress status of minute bone union by improving X-ray permeability.

Further, it is possible to provide strong adhesive strength so as to prevent bending phenomenon of each joint and bent portion of a human body and sufficiently endure a weight of the human body by configuring a rigidity reinforcing means in a support and a skin protector to allow a user to more conveniently use the medical cast.

Moreover, it is possible to interrupt occurrence of secondary infection by preventing an injury which occurs on the skin of the patient by a cutter blade at the time of removing the cast and an injury which occurs due to direct friction between the medical cast and the skin.

Besides, the medical cast manufactured in a stocking type is provided to manufacture the medical cast with various patterns and colors.

DESCRIPTION OF DRAWINGS

FIGS. 1 to 3 are diagrams illustrating a medical cast according to a first preferred embodiment of the present invention.

FIG. 4 is a cross-sectional view of the principal part illustrating the medical cast according to the first preferred embodiment of the present invention.

FIG. 5 is a diagram illustrating a wearing process of the medical cast according to the first preferred embodiment of the present invention.

FIG. 6 is a diagram illustrating a medical cast according to a second preferred embodiment of the present invention.

FIG. 7 is a diagram illustrating a wearing process of the medical cast according to the second preferred embodiment of the present invention.

FIG. 8 is a diagram illustrating a medical cast according to a third preferred embodiment of the present invention.

BEST MODE

Hereinafter, preferred embodiments of the present invention will be described in detail with reference to the accompanying drawings. When reference numerals refer to components of each drawing, it is noted that although the same components are illustrated in different drawings, the same components are referred to by the same reference numerals as possible. Further, in the description of the present invention, the detailed descriptions of known related constitutions or functions thereof may be omitted if they make the gist of the present invention unclear.

FIGS. 1 to 3 are diagrams illustrating a medical cast according to a first preferred embodiment of the present invention, FIG. 4 is a cross-sectional view of the principal part illustrating the medical cast according to the first preferred embodiment of the present invention, FIG. 5 is a diagram illustrating a wearing process of the medical cast according to the first preferred embodiment of the present invention, FIG. 6 is a diagram illustrating a medical cast according to a second preferred embodiment of the present invention, FIG. 7 is a diagram illustrating a wearing process of the medical cast according to the second preferred embodiment of the present invention, and FIG. 8 is a diagram illustrating a medical cast according to a third preferred embodiment of the present invention.

As illustrated in FIGS. 1 to 3, the medical cast of the present invention which is used for protecting a bone fracture portion of an arm or a leg among body parts is configured to include a skip protector 100 and a cast constituted by an inner supporting cast 200 and an outer supporting cast 300.

The skin protector 100 is configured to improve elasticity of a joint portion such as a wrist or an ankle among body parts where an operation is performed, maximize adhesive strength with a skin, and easily absorb and discharge moisture and manufactured by mixing at least two kinds of functional fibers including polyester yarn, span covering yarn, polyolefin, polypropylene yarn, core tax, and olefin yarn so as to improve air permeability and manufactured such that diamond-shaped mesh holes are formed in the shape of a meshed net to be manufactured with the elasticity and restorability so as to secure a uniform ventilation hole and smoothly circulate blood.

The skin protector 100 may be configured to have sterilization and an antibacterial property in a fiber itself by combining the functional fiber and a sterilizer and an antibacterial agent and mixing a waterproof agent in order to prevent minute bacteria on the surface of the fiber.

Moreover, the skin protector 100 of the present invention is configured in a dual structure constituted by an inner layer 110 and an outer layer 120, and thus, the inner layer 110 is configured to come in direct contact with a skin of a user, that is, a patient and the outer layer 120 is configured to come in contact with a cotton yarn forming an inner surface of any one of the inner supporting cast 200 and the outer supporting cast 300 of the cast to thereby protect the skin of the patient by means of the inner layer 110 and cover shock by damage heat from the outer layer 120 and prevent an inflow of foreign substances.

The inner supporting cast 200 is a component that is configured to cover the skin protector 100 or the skin of the patient and provide primary rigidity while allowing the skin protector 100 to be more closely attached to the skin of the patient.

That is, the inner supporting cast 200 of the present invention is configured in the dual structure and constituted by an inner surface supporting cast 202 and an outer surface supporting cast 204. The inner surface supporting cast 202 is configured to come into direct contact with the skin of the patient and the outer surface supporting cast 204 is configured to come into contact with the cotton yarn forming the inner surface of the outer supporting cast 300 of the medical cast. Thus, the inner surface supporting cast 202 forming the inner surface of the inner supporting cast 200 is configured in the same configuration as the skin protector 100 and configured to simultaneously perform a role of the skin protector 100. The medical cast of the present invention may selectively use the skin protector 100 according to an affected area location or a bone fracture degree of the patient and further shorten a time of the operation.

The inner surface supporting cast 202 of the inner supporting cast 200 may prevent various germs from being bred by preventing sweat or body waste from remaining between the casts to minimize various infections, urtication, red spots, and pains.

Further, the outer surface supporting cast 204 of the inner supporting cast 200 is configured to cover an outer surface of the inner surface supporting cast 202 to form an inner ventilating channel 210 for improving the air permeability and a plurality of at least two adhesion reinforcing units 240 that improves the elasticity of the cast are configured at the joint portion of the patient.

Herein, the inner ventilating channel 210 is formed by the diamond-shaped mesh holes having the shape of a meshed net and the mesh hole is preferably manufactured with an area of 0.6 mm, but the area of the mesh hole is not limited thereto.

Moreover, spinning ends 250 are configured on upper and lower ends of the outer surface supporting cast 204, which is formed by the span yarn to provide a predetermined elastic pressure, thereby stably fixing the inner supporting cast 200 to the affected area of the user or the skin protector 100.

Further, an inner rigidity reinforcing unit 220 is configured on one surface of the outer surface supporting cast 204, which elongates in the longitudinal direction and provides the primary rigidity of the medical cast and the inner rigidity reinforcing unit 220 is fixed to the inner ventilating channel 210 and the inner surface supporting cast 202 at both sides thereof through an inner molding unit 230.

That is, the inner ventilating channel 230 allows the inner surface supporting cast 202 and the outer surface supporting cast 204 constituting the inner supporting cast 200 to be integrally configured and fixes the inner rigidity reinforcing unit 220 having high elasticity to stably fix the affected area or the joint portion of the patient.

In particular, in the case where the affected area of the patient is a portion on which the weight of the human body concentrates, such as the angle and the leg, the weight which concentrates on the affected area of the patient is distributed through the inner rigidity reinforcing unit 220 by pulling the inner rigidity reinforcing unit 220 outward from the center of the inner molding unit 230 to more rapidly treat the affected area of the patient.

The inner supporting cast 200 of the present invention, which is configured as above may be manufactured in various shapes including a pipe shape, a heck-shape, a trapezoidal shape, a pot shape, a fan shape, a tube type, an arm type, a leg shape, and the like according to a body structure of the patient.

The outer supporting cast 300 is configured to cover the inner supporting cast 200 and is impregnated with a hardening solution having hydraulic properties to perform the hardening, and comprising an outer ventilating channel 310 formed along the circumference thereof, a plurality of one or more adhesion enhancing parts are configured to be spaced apart from each other at a predetermined interval in the longitudinal direction of the outer ventilating channel 310 so that the joint portion of the patient conveniently moves by providing predetermined elastic force through connection with the outer ventilating channel 310.

Herein, the outer ventilating channel 310 is manufactured by mixing two or more functional fibers such as polyester yarn, span covering yarn, polyolefin, polypropylene yarn, gore tex, and olefin yarn and is formed by the diamond-shaped mesh holes having the shape of a meshed net and the mesh hole is preferably manufactured with an area of 0.2 to 0.5 mm, but the area of the mesh hole is not limited thereto.

Further, spinning ends 350 are configured on the outer supporting cast 300, which fixes the medical cast on upper and lower ends thereof similarly to the inner supporting cast 200.

Moreover, the cutter blade comes in contact with one outer surface of the outer supporting cast 300 in order to remove the medical cast, a cutter unit 360 is formed, which prevents the injury from being generated at the skin of the patient or the affected area at the time of removing the medical cast by guiding the progressing direction of the cutter blade, and an outer rigidity reinforcing unit 320 providing secondary rigidity of the medical cast and an outer molding unit 330 molding the outer rigidity reinforcing unit 320 while reinforcing the rigidity of the outer supporting cast 300 are configured at both sides of the cutter unit 360.

The outer support cast 300 of the present invention, which is configured as above is formed in the same shape as the inner supporting cast 200 and manufactured in various shapes including the pipe shape, the heck shape, the trapezoidal shape, the pot shape, the fan shape, the arm shape, the leg shape, and the like according to the body structure of the patient.

Meanwhile, on an outer surface of the outer supporting cast 300 of the present invention, at the time of manufacturing the outer ventilating channel 310, phrases and decorations with one or more types of various colors or formed with various designs are woven to provide a more elegant medical cast.

The medical cast of the present invention, which is configured as above is worn while the skin protector 100 or the inner supporting cast 200 covers the affected area of the patient and thereafter, the outer supporting cast 300 is worn while dually winding an outer portion of the inner supporting cast 200 to significantly shorten the operation time of the medical cast and provide a comfortable wearing sense by providing an uniform pressure regardless of the affected area of the patient, as illustrated in FIG. 5.

The inner supporting cast 200 and the outer supporting cast 300 are integrally configured through a connection line 410 connecting the spinning end 250 configured on the top of the inner supporting cast 200 and the spinning end 350 configured on the top of the outer supporting cast 300 to be configured to be symmetric to each other, and as a result, the medical cast configured dually is formed by inserting the inner supporting cast 200 into the inner surface of the outer supporting cast 300 during the operation and thereafter, the inner supporting cast 200 is worn while being rolled up outward the affected area of the patient or the skin protector 100 to thereby further shortening the operation time of the medical cast.

In particular, as illustrated in FIG. 6, when the bone fracture portion of the patient occurs at a lower body side, that is, a knee, the ankle, a toe, and the like, an ankle portion and a heel portion are formed to be integrally configured, and as a result, a shape thereof becomes the shape of socks to improve a protection effect of the bone fracture portion of the patient and furthermore, cast weaving shapes of the ankle portion and the heel portion are formed to be woven with shapes corresponding thereto to prevent the inner supporting cast 200 and the outer supporting cast 300 from being overlapped with each other. Therefore, the cast is easily operated to conveniently wear the cast.

Further, as illustrated in FIG. 8, a detachable unit 510 may be configured in any one of the inner supporting cast 200 and the outer supporting cast 300 of the present invention.

Herein, if the detachable unit 510 has predetermined adhesive force and is harmless to the human body, any one may be used as the detachable unit 510, but in the present invention, the detachable unit 510 is configured by a Velcro tape to be woven to cover the affected area of the patient, thereby significantly shortening the operation time of the medical cast and providing the comfortable wearing sense by providing the uniform pressure regardless of the affected area of the patient.

That is, when the detachable unit 510 of the present invention is configured in the inner supporting cast 200, a contact with the affected area of the patient may be minimized and the pressure applied to the affected area is uniformly provided to conveniently wear the cast and a large adhesive strength so as to prevent a bending phenomenon from being occurred at each joint and bending portion.

Further, when the detachable unit 510 is configured in the outer supporting cast 300, the operation time of the medical cast may be significantly shortened and the comfortable wearing sense may be provided by providing the uniform pressure regardless of the affected area of the patient.

Moreover, at the time of manufacturing the skin protector 100, the medical cast of the present invention prevents dust bacteria, air floating bacteria which causes atopic dermatitis, pathogenic bacteria, and mutational bacteria from being bred on the contact part with the skin of patient such that far-infrared ray is input so as to prevent a disease such as urtication and further maximize a treatment effect.

That is, when manufacturing of the skin protector 100 of the present invention is completed, the skin protector 100 is input in a far-infrared ray generator or an inorganic mineral substance is finely pulverized or liquefied to be input in the skin protector 100, and as a result, as the far-infrared ray may penetrate the skin protector 100, when the patient wears a product, the bone fracture portion may be joined and various injuries and diseases may be effectively treated.

In this case, any one of synthetic zeolite, $TiO_2$, rutil, anatase, brookite, Ca, natural mineral, and sericite which have particle size of 2 to 5 μm or synthetic photocatalyst in which two or more are mixed are mixed in the amount of a predetermined weight and a mixed mixture composition is applied onto the surface of the skin protector 100 to radiate the far-infrared rays.

Meanwhile, the mixture composition is composed of mixture compositions in which synthetic zeolite of 10 to 40 wt %, $TiO_2$ of 5 to 8 wt %, rutil of 8 to 10 wt %, anatase of 12 to 17 wt %, brookite of 15 to 20 wt %, Ca of 7 to 14 wt %, natural mineral of 5 to 8 wt %, and sericite of 8 to 13 wt % in terms of a total weight are mixed.

Further, synthetic photocatalysts which are divided into 0.2 to 0.3 μm are used to be mixed with synthetic zeolite and when the mixing is completed, the mixture composition is input in the far-infrared ray generator to be applied and dried to preferably radiate synthetic zeolite, synthetic photocatalysts, and the far-infrared ray, but the present invention is not limited thereto.

The above description just illustrates the technical spirit of the present invention and various modifications and transformations can be made by those skilled in the art without departing from an essential characteristic of the present invention. Accordingly, the exemplary embodiments disclosed herein are intended to not limit but describe the technical spirit of the present invention but the scope of the technical spirit of the present invention is not limited by the exemplary embodiments. The scope of the present invention should be interpreted by the appended claims and all technical spirit in the equivalent range thereto should be interpreted to be embraced by the claims of the present invention.

The invention claimed is:

1. A medical cast comprising:
    a skin protector coming into contact with the affected area of a patient, woven by mixing and using at least two kinds of functional fibers, including polyester yarn, span covering yard, polyolefin, polypropylene yarn, gore tex, or olefin yarn, in order to increase adhesive strength with the skin, and manufactured such that diamond-shaped mesh holes are formed in the shape of a meshed net;
    an inner supporting cast formed to cover the outer side of the skin protector and comprising an inner surface supporting cast for absorbing sweat or body waste between the casts, an inner ventilating channel for covering the outer surface of the inner surface supporting cast and improving air permeability, an adhesion enhancing part for increasing the elasticity of the cast at a joint of the patient, and an inner rigidity reinforcing part for providing primary rigidity for the medical cast; and
    an outer supporting cast formed to cover the outer side of the inner supporting cast, impregnated with a hardening solution having hydraulic properties, and comprising an outer ventilating channel (310) formed along the circumference thereof, an adhesion enhancing part connected with the outer ventilating channel (310) so that the joint of the patient conveniently moves by providing predetermined elastic force, a cutter part provided on one surface of the outer side thereof for guiding a progressing direction of a cutter blade, and outer rigidity reinforcing parts formed on both sides of the cutter part so as to provide secondary rigidity for the medical cast said adhesion enhancing parts for said inner supporting cast and said outer supporting cast overlaps each other, said inner ventilating channel and said outer ventilating channel overlaps each other when placed on a patient, said cutter part extends whole length of the medical cast, wherein the inner rigidity reinforcing unit further includes inner molding units to be fixed with the inner ventilating channel and the inner surface supporting cast on both sides thereof.

2. The medical cast of claim 1, wherein the inner and outer ventilating channels are formed by the meshed net-shaped diamond-shaped mesh holes and the mesh holes are manufactured in an area of 0.6 mm and 0.2 to 0.5 mm, respectively.

3. The medical cast of claim 1, wherein spinning ends formed by span yarn to provide a predetermined elastic pressure are configured on upper and lower ends of the outer supporting cast and the outer surface supporting cast.

4. The medical cast of claim 1, wherein the outer rigidity reinforcing unit further includes outer molding units to be fixed with the outer ventilating channel and the cutter unit on both sides thereof.

5. The medical cast of claim 1, wherein two or more of a color, a phrase, and a decoration are configured on the surface of the outer supporting cast.

6. The medical cast of claim 1, wherein the inner supporting cast and the outer supporting cast are integrally connected to each other by a connection line so as to have opposite locations to each other to be symmetric to each other.

7. The medical cast of claim 1, wherein a detachable unit having predetermined adhesive strength is configured in any one of the inner supporting cast and the outer supporting cast to be worn while covering the affected area of the patient.

8. The medical cast of claim 1, wherein the inner supporting cast and the outer supporting cast are manufactured in any one of a pipe shape, a heck-shape, a trapezoidal shape, a pot shape, a fan shape, a tube type, an arm type, and a leg shape according to a body structure of the patient.

9. The medical cast of claim 1, wherein the skin protector is constituted by an inner layer which comes in direct contact with the skin of the patient and an outer layer which comes in contact with cotton yarn forming an inner surface of any one of the inner supporting cast and the outer supporting cast.

10. The medical cast of claim 1, wherein the skin protector, and the inner and outer supporting casts are combined with a sterilizer and an antibacterial agent and mixed with a waterproof agent in order to prevent micro bacteria from being grown.

11. The medical cast of claim 1, wherein the functional fiber is any one of polyester yarn, span covering yarn, polyolefin, polypropylene yarn, gore tex, and olefin yarn.

12. The medical cast of claim 1, wherein in the skin protector, synthetic zeolite and synthetic photocatalysts are mixed at a predetermined ratio and the mixed mixture composition is input in a far-infrared ray generator so as to be applied and dried on the surface of the skin protector to radiate synthetic zeolite, synthetic photocatalysts, and far-infrared rays.

13. The medical cast of claim 12, wherein the synthetic zeolite has a particle size of 2 to 5 µm.

14. The medical cast of claim 12, wherein in the synthetic zeolite and the synthetic photocatalysts, synthetic zeolite of 10 to 40 wt %, $TiO_2$ of 5 to 8 wt %, rutil of 8 to 10 wt %, anatase of 12 to 17 wt %, brookite of 15 to 20 wt %, Ca of 7 to 14 wt %, natural mineral of 5 to 8wt %, and sericite of 8 to 13 wt % in terms of a total weight are mixed.

15. The medical cast of claim 12, wherein the synthetic photocatalysts are finely pulverized into 0.2 to 0.3 µm.

\* \* \* \* \*